United States Patent [19]

Stoll

[11] Patent Number: 4,538,467
[45] Date of Patent: Sep. 3, 1985

[54] METHOD AND APPARATUS FOR MEASURING THE STRENGTH OF HARDENED CONCRETE

[76] Inventor: Ulrich W. Stoll, 2121 Hall, Ann Arbor, Mich. 48104

[21] Appl. No.: 568,863

[22] Filed: Jan. 6, 1984

[51] Int. Cl.³ .............................................. G01N 33/38
[52] U.S. Cl. ...................................................... 73/803
[58] Field of Search .................. 73/768, 803, 845, 843

[56] References Cited

U.S. PATENT DOCUMENTS 3,861,201  1/1975  Kaindl .................................. 73/803

Primary Examiner—Donald O. Woodiel
Attorney, Agent, or Firm—Stephenson and Boller

[57] ABSTRACT

A method and apparatus for measuring the in situ strength of concrete containing aggregate particles of varying sizes in which a test member having at least one reacting surface is placed in the path of the concrete when the concrete is in the plastic state so that when the concrete is hardened, the test member is embedded therein. A force is then applied to the test member after the concrete has hardened tending to move the test member so as to cause the reacting surface to exert a compressive force on a portion of the hardened concrete of sufficient magnitude to create a rupture surface in the concrete. The large aggregate particles are screened out of the expected location in the concrete of the rupture surface so that large aggregate will not affect the test results.

3 Claims, 7 Drawing Figures

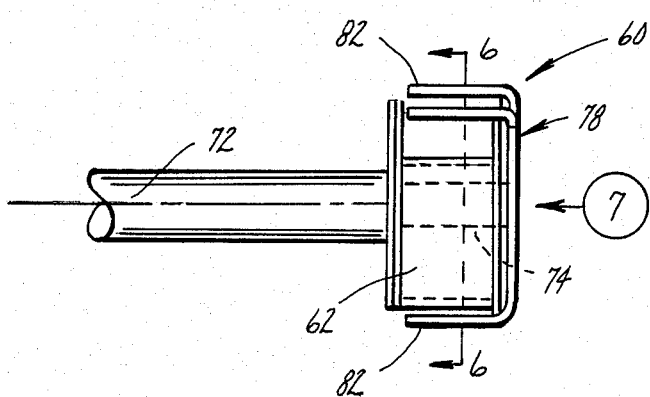
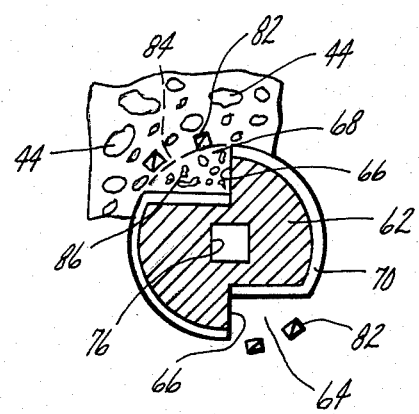
fig. 5        fig. 6
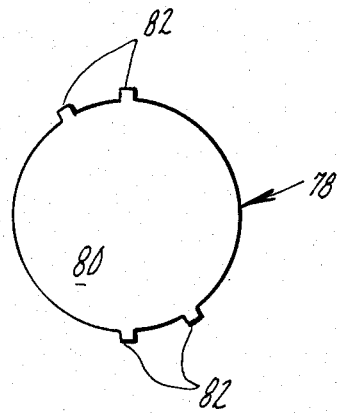
fig. 7

METHOD AND APPARATUS FOR MEASURING THE STRENGTH OF HARDENED CONCRETE

BACKGROUND OF THE INVENTION

In construction projects utilizing concrete structural members such as cast-in-place reinforced concrete beams or columns, it is important that the builder be able to ascertain the in situ compressive strength of the beams or columns. A common method for determining the strength of concrete structural members is the "pull-out" test in which a cylindrical metal test member having a stem projecting from one side is temporarily mounted on a concrete form so that it projects into the area to be filled with plastic concrete. The plastic concrete then envelopes the test member, and after the concrete is hardened, at the desired moment, tension is applied to the stem to induce pull-out failure in compression of the concrete. The force required to induce pull-out failure is related to the compression strength of the concrete.

A second test method is disclosed in my U.S. Pat. No. 4,425,801, issued Jan. 17, 1984. This apparatus consists of a generally cylindrical or disk-shape test member which is provided on its periphery with at least one notch so as to form a generally radially extending reactive surface which engages the adjacent concrete when the cylinder is rotated. A step attached to one face of the test member constitutes the means for applying a torque to the test member so as to engage the reactive surface with the adjacent concrete. In this latter method, the magnitude of the torque required to induce compressive failure in the hardened concrete is related to the compression strength of the concrete.

In both test methods, large aggregate particles encroaching on the anticipated rupture surfaces will also affect the accuracy of the test results. It is an object of this invention, therefore, to provide an improved method and apparatus for measuring the strength of hardened concrete in which a shield or screen is provided to prevent the encroachment of large aggregate particles in the portion of the concrete structure adjacent the reactive surfaces on the test members.

SUMMARY OF THE INVENTION

This invention provides an improved method and apparatus for measuring the strength of brittle material such as concrete in which a test member is embedded in the material while it is in a plastic state and a measurable force, either a turning force or a pulling force, is applied to the test member after the concrete is hardened. The test member is of generally cylindrical or disk shape, although the invention is not limited to a test member of any particular size or shape, and includes a reacting surface thereon operable to exert a compressive force on a portion of the hardened concrete in response to the force applied to the test member. The applied force is increased to a magnitude at which the concrete ruptures, thereby creating a rupture surface. A shield member, preferably shaped to slip over and be held weakly on the test member, has a screen or filter portion which has openings or passages of sufficient size to permit the plastic concrete to pass therethrough and extend into the anticipated rupture area of the concrete. However, the shield member prevents the encroachment of large particles of aggregate from passing into proximity to the reacting surface thereby insuring relatively uniform test results with the method and apparatus of this invention.

It can thus be seen that by virtue of the combination of the shield member with the test member in the method and apparatus of this invention relatively uniform test results are assured because the affects of large aggregate particles are eliminated.

Further objects, features, and advantages of this invention will become apparent from a consideration of the following description and the appended claims when taken in connection with the accompanying drawing in which:

FIG. 5 is a side elevational view of a test member that is operated by a turning force, showing the shield member of this invention in assembly relation therewith;

FIG. 6 is a sectional view of the apparatus shown in FIG. 5, as seen from substantially the line 6—6 in FIG. 5, and diagrammatically illustrating concrete with small and large aggregate particles in proximity to the test member; and FIG. 7 is an end view of the structure shown in FIG. 5 as seen from the arrow "7" in FIG. 5.

Figure 1:
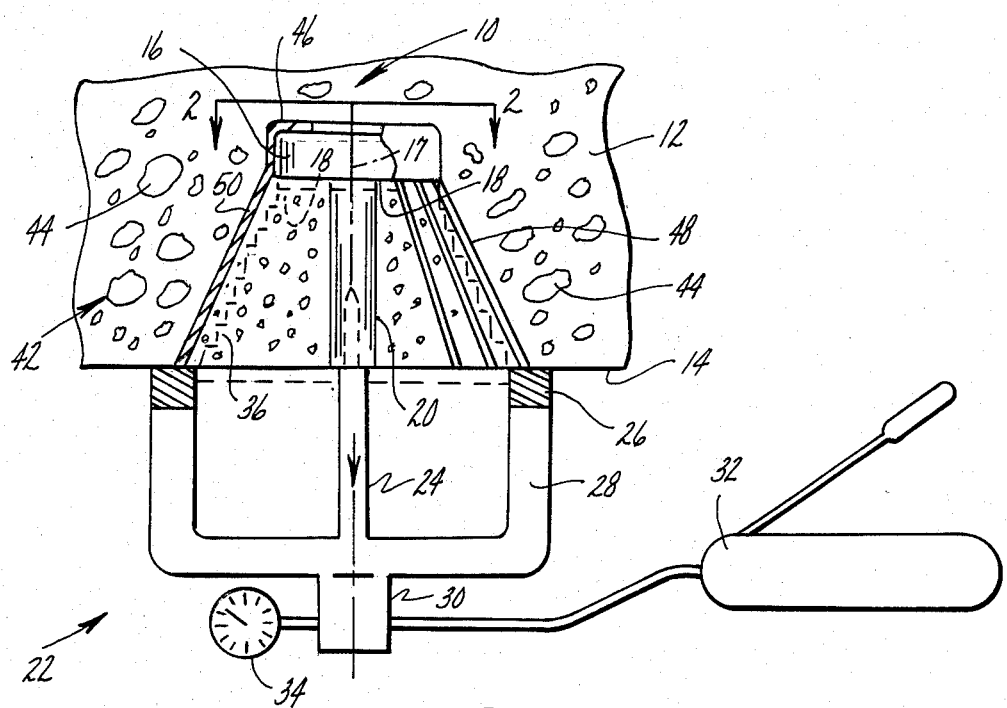
FIG. 1 is a side elevational view of a "pull-out" test apparatus showing the shield member of this invention in assembly relation therewith and diagrammatically illustrating concrete with small and large aggregate particles in proximity to the test member.
Figure 2:
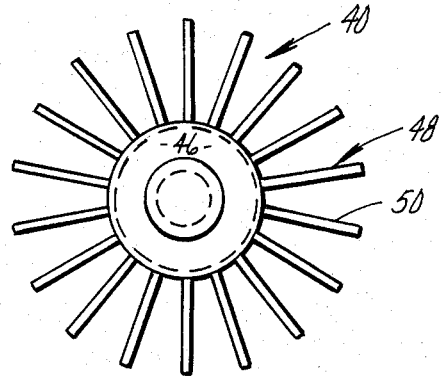
FIG. 2 is a view of one end of the apparatus shown in FIG. 1 as seen from substantially the line 2—2 in FIG. 1.

With reference to the drawing, the apparatus of this invention, indicated generally at 10, is illustrated embedded in a concrete structure 12 having an outer or accessible face 14. The apparatus 10 includes a test member 16, generally cylindrical or disk-like in shape having an axis 17 and a bearing or reacting surface 18 on one side generally perpendicular to the axis 17. An elongated stem 20 of a length substantially equal to or slightly exceeding the diameter of the test member 18, is secured to the surface 18 and extends along the axis 17.

A pulling force is applied to the stem 20 by a hydraulic jack 22 that includes a spindle 24 threadably connected to the stem 20 and an annular bearing ring 26 of a diameter substantially greater than the diameter of the test member 16. The bearing 26 is supported on a yoke 28 and the spindle 24 and the yoke 28 are connected to a piston and cylinder assembly 30 that is operable by a pump 32 to exert a pulling force on the spindle 24 and apply a compressive force to the bearing ring 26 holding it firmly against the concrete structure face 14. A gauge 34 provides a continuous measurement of the magnitude of the pulling force applied by the spindle 24 to the test member 16.

In the use of the apparatus 10, the pump 32 is .operated to continually increase the magnitude of the pulling force on the spindle 24 until the compressive force of the reaction or bearing surface 18 on the test member 16 causes rupture of the adjacent portion of the structure 12. Such rupture creates a rupture surface 36 which is generally frusto conical in shape extending from the outer periphery of the test member surface 18 to the approximate inner edge of the bearing ring 26.

In the improved apparatus of this invention, a shield member 40 is assembled with the test member 16 prior to pouring of the plastic concrete which subsequently hardens and forms the brittle structure 12. As shown in FIG. 1, the concrete contains aggregate 42 of varying size, including large particles 44. By large particles, is meant particles that are larger than about 3/16″ in diameter or if irregularly shaped larger than 3/16″ in their largest dimension. The function of the shield 40 is to prevent nearly all of the large aggregate particles 44 from encroaching on the anticipated rupture surface 36.

A heretofore inherent problem with the test apparatus 10 and its application is the anomalous and spurious higher resistance to pull-out which occurs should larger aggregate particles or stones be lodged against the bearing surface 18 of the test member 16 or across the potential failure surface 36. This may and often does occur in the course of placing the plastic concrete around and adjacent to the member 16. Depending on the size, number, and degree of such encroachment and depending on the strength of aggregate relative to the prevailing strength of the mortar at time of test, the resultant pull-out resistance may be more or less greater than that associated with resistance of the controlling mortar and its associated unconfined cylinder strength. The current expedient is to perform a relatively large number of duplicate pull-out tests (i.e., 10 or more) and "cast out" those test values which are deemed spurious (i.e., high) and rely on the hope that the bulk of the test values are not inordinately affected by aggregate interference.

The shield member 40 includes an annular mounting section 46 which is supported on the test member 16 and a screen section 48 which is generally frusto conical in shape and is positioned outwardly and in an encompassing relation with the anticipated rupture surface 36. The screen section 48 is formed by a plurality of elongated spaced apart fingers 50 which radiate downwardly and outwardly in a diverging relation from the support section 46. A large aggregate particle 44 will be unable to pass between adjacent fingers 50, but the plastic concrete can readily flow through the spaced between the fingers 50.

Figure 3:
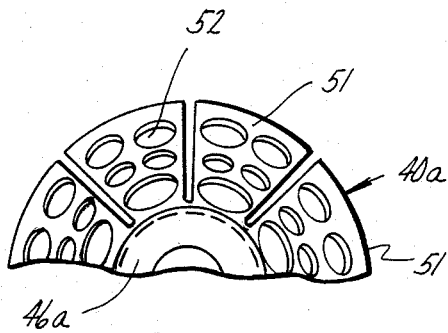
FIGS. 3 and 4 are views like FIG. 2 of modified forms of the shield member of this invention.

A modified form of shield member 40a is illustrated in FIG. 3 having a support section 46a and downwardly and outwardly inclined sheet metal segments 51 which are spaced apart and formed with round openings 52 of a size to prevent the passage therethrough of the large aggregate particles 44 but readily permit the flow of plastic mortar therethrough.

Figure 4:
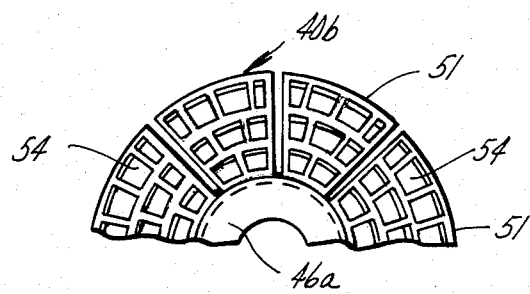

Another modified form of the shield member 40 is shown in FIG. 4 and indicated generally at 40b. The member 40b is identical to the member 40a and like numerals are used thereon to indicate like parts, except that the openings 54 in the segments 50 are generally rectangular rather than round as in the member 40a.

In the use of the apparatus 10 with a shield member 40, 40a or 40b, there is assurance that the potential failure surface 36 will not be transfixed by large aggregate 44. Consequently, the variablility of pull-out resistance of the concrete will be reduced from the tests that were heretofore performed where varying amounts and sizes of aggregate transfix the failure surface 36, and that also, spurious, high pull-out resistance due to encroachment by larger aggregate particles in proximity to the reaction surface 18 is precluded.

The advantages obtained by use of the screen 40 with the pull-out test member 16 are also obtainable in torque type test apparatus of the type indicated generally at 60 in FIG. 5 and 6. The apparatus 60 includes a test member 62 of cylindrical or disk-like shape described in detail in my patent 4,425,801. The test member 62 is provided with a pair of diametrically opposite notches 64 which form a pair of radially extending reacting or bearing surfaces 66 which will bear against the concrete 68 when the test member 62 is rotated in a counterclockwise direction as viewed in FIG. 6. A layer 70, of yieldable resilient material, such as rubber, polyurethane, or polyethylene, is provided on the outer surface of the test member 62, except for the reaction surfaces 66.

Torque is applied to the test member 62 by a rotatable shaft or rod 72 which has a square end portion 74 that extends through a square opening 76 in the test member 62. A shield member 78 has a supporting portion 80 that is telescoped over the outer end of the test member 62 and terminates in inwardly extending pairs of fingers 82 which extend over the notches 64 as shown in FIG. 6. The fingers 82 perform the same function as the fingers 50 heretofore described, namely, keeping the large aggregate particles 44 from entering the notches 64.

Accordingly, when plastic concrete is poured to create a structure such as the structure 12, the test member 62 is first located in the path of the plastic concrete which readily flows between the fingers 82 so as to fill the notches 64. After the concrete has hardened the strength is tested by rotating the test member 62, with the shaft 72, in a counterclockwise direction as viewed in FIG. 6, so that the reaction surfaces 66 will create a compressive force on the concrete in the notices 64. The magnitude of the turning force on the test member 62 is increased until the concrete is ruptured. When rupture occurs, rupture surface 84 will be created outside each of the notches 64, each surface 84 being arcuate in shape so that a piece of concrete in the shape of a convex cusp 86 will be created in each of the notches 64.

By virtue of the shield member 78, uniform test results, like those heretofore described in connection with the apparatus 10, will be achieved with the use of the apparatus 60. The screen member 80 is generally cup shaped so that it can be slipped over and held weakly on the cleated test member 62 so that the fingers 82 will extend over the notches 64 allowing the plastic mortar to pass between the fingers 82 while keeping large aggregate particles 44 from encroaching on the anticipated fracture surface 84.

From the above description it is seen that this invention provides improved method and apparatus for testing the compressive strength of concrete which provides improved results from the standpoint of uniformity by virtue of the exclusion of large aggregate particles 44 from encroaching on the anticipated fracture surface.

What is claimed is:

1. An apparatus for determining the compressive strength of hardened concrete, a test member adapted to be enveloped in concrete in the plastic state, said test member having a bearing surface engageable with the concrete after hardening, means operatively associated with said test member capable of moving said bearing surface with sufficient force to cause fracture of said hardened concrete, the improvement comprising a shield member operatively associated with said test member so as to restrict the passage of larger particles of aggregate in said plastic concrete into positions in proximity to said bearing surface so as to affect the fracture of said hardened concrete, said test member being generally cyclindrical in shape and having an axis bearing surface generally perpendicular to said axis, and wherein said means for moving said bearing surface is operable to move said bearing surface in a direction generally parallel to said axis, said shield member comprising a mounting section supported on said test member and finger members positioned around said bearing surface and extending away therefrom in a generally deverging arrangement.

2. An apparatus for determining the compressive strength of hardened concrete, a test member adapted to be enveloped in concrete in the plastic state, said test member having a bearing surface engageable with the concrete after hardening, means operatively associated with said test member capable of moving said bearing surface with sufficient force to cause fracture of said hardened concrete, the improvement comprising a shield member operatively associated with said test member so as to restrict the passage of larger particles of aggregate in said plastic concrete into positions in proximity to said bearing surface so as to affect the fracture of said hardened concrete, said test member being generally cylindrical in shape and having an axis of rotation and at least one bearing surface extending radially outwardly from said axis, said shield member extending circumferentially around said cylindrical body and having restricted openings therein to limit the size of aggregate that can pass therethrough into proximity to said bearing surface.

3. In a method for measuring the compressive strength of hardened concrete containing aggregate particles of varying sizes in which a test member having a reacting surface is placed in the path of the concrete when in the plastic state so that when the concrete is hardened said test member is embedded therein, and a force is applied to said test member tending to move said test member so as to cause said reacting surface to exert a compressive force on said hardened concrete of sufficient magnitude to create a rupture surface in said concrete; the improvement comprising screening out large aggregate particules from the expected surface, said force on said test member being a turning force creating in said concrete an arcuate rupture surface and said screening being accomplished by locating a shield member having openings therethrough of restricted size radially outwardly of and adjacent the expected location in said concrete of said arcuate rupture surface.

* * * * *